United States Patent [19]

Watanabe et al.

[11] 4,160,823

[45] Jul. 10, 1979

[54] TRANSPARENT HAIR RINSING COMPOSITION

[75] Inventors: Hiroshi Watanabe; Toshihiro Shirose, both of Funabashi; Eiji Iijima, Sakura, all of Japan

[73] Assignee: Kao Soap Co., Ltd., Tokyo, Japan

[21] Appl. No.: 774,257

[22] Filed: Mar. 4, 1977

[30] Foreign Application Priority Data

Mar. 29, 1976 [JP] Japan .................................. 51-34764

[51] Int. Cl.² ........................ A61K 7/06; A61K 7/09; C11D 1/62
[52] U.S. Cl. ........................................ 424/70; 424/71; 252/547
[58] Field of Search ........................ 424/70, 71, 173; 252/547

[56] References Cited

U.S. PATENT DOCUMENTS

| | | | |
|---|---|---|---|
| 3,322,676 | 5/1967 | Hiestand et al. | 424/70 |
| 3,563,901 | 2/1971 | Crothy | 424/70 UX |
| 3,609,102 | 9/1971 | Schlossman | 424/173 |
| 3,761,429 | 1/1973 | Yamano et al. | 252/547 |
| 3,862,045 | 1/1975 | Sato et al. | 252/547 |
| 3,892,669 | 7/1975 | Ropesorda et al. | 252/547 |
| 3,959,157 | 5/1976 | Mamorato | 252/547 |

*Primary Examiner*—Donald B. Moyer
*Attorney, Agent, or Firm*—Blanchard, Flynn, Thiel, Boutell & Tanis

[57] ABSTRACT

A transparent liquid hair rinsing composition consisting essentially of 0.1 to 10 weight percent of a quaternary ammonium salt, 0.1 to 10 weight percent of an ethoxylated alcohol or alkyl phenol, 5 to 30 weight percent of a solvent and water.

7 Claims, No Drawings

TRANSPARENT HAIR RINSING COMPOSITION

BACKGROUND OF THE INVENTION

1. Field of the Invention

The present invention relates to a transparent hair rinsing composition which is excellent in rinseability and which imparts good smoothness, good suppleness and good feel to hair. More particularly, the present invention relates to a hair rinsing composition which possesses excellent transparency and stability and is characterized by a reduced solvent content. The hair rinsing composition comprises as critical ingredients (A) a quaternary ammonium salt, and (B) at least one member selected from (1) polyoxyethylene alkyl and alkenyl ethers in which the average value of the number of moles of ethylene oxide added is in the range of from 1 to 7, the unreacted alcohol content is lower than 3% and the carbon number of the alkyl or alkenyl group is in the range of from 8 to 20 and (2) polyoxyethylene alkylphenyl ethers in which the average value of the number of moles of ethylene oxide added is in the range of from 1 to 7, the unreacted alcohol content is lower than 3% and the carbon number of the alkyl group is in the range of from 6 to 12.

2. Description of the Prior Art

Hair rinsing compositions comprising, as an effective component, a quaternary ammonium salt such as distearyl dimethyl ammonium chloride have heretofore been used for minimizing such undesirable phenomena as breaking, entanglement, static charging and difficulty in the combing of washed hair. A hair rinsing agent should impart softness, smoothness and an antistatic property to washed hair. If a quaternary ammonium salt alone is employed, no satisfactory effects can be obtained with respect to softness and smoothness. Accordingly, in order to obviate this defect, oils and fats such as higher alcohols, glycerides and liquid paraffin have heretofore been incorporated in hair rinsing compositions. Hair rinsing compositions in which such oils and fats are incorporated have, in general, an opaque or pearlescent appearance.

If it is possible to form a transparent liquid when such an oily and fatty substance is used, the resulting hair rinsing composition will have a characteristic appearance and a high commercial value. Various attempts have heretofore been made to attain this goal. A most popular method comprises incorporating in a hair rinsing agent an organic solvent such as ethyl alcohol, isopropyl alcohol, ethylene glycol, propylene glycol or the like in as large an amount as 60 wt.% or more, thereby to solubilize the above-mentioned oily and fatty substance and to render the composition transparent. In addition, there can be mentioned a method in which oils and fats are solubilized by using a large amount of a highly hydrophilic non-ionic surface active agent obtained by adding 20 to 40 moles of ethylene oxide to a higher aliphatic alcohol. Moreover, there has been proposed a hair rinsing composition free of such oils and fats, which is comprised of an aqueous solution of a special water-soluble cationic surface active agent having the formula:

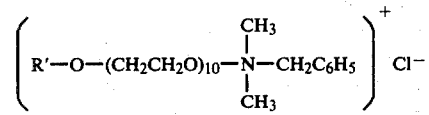

-continued
or

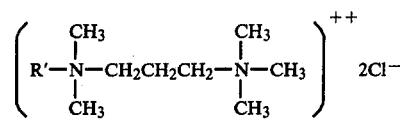

wherein R' is alkyl having 16 to 18 carbon atoms.

Transparent hair rinsing compositions formed by solubilizing cationic surface active agents and oils and fats by using large quantities of organic solvents are disadvantageous because of their very high manufacturing cost. Further, the method comprising solubilizing oils and fats by using large quantities of highly hydrophilic non-ionic surface active agents is not fully satisfactory because it is difficult to maintain the resulting transparent solution system in a stable condition and the use of a large amount of a non-ionic surface active agent results in a drastic reduction of the desired rinsing effect. When there is used an aqueous solution of a special water-soluble cationic surface active agent alone, even though a transparent composition can be obtained, the product does not have a satisfactory rinsing effect. As will be apparent from the foregoing discussion, there has not been developed a transparent hair rinsing composition which has a high rinsing effect and which can be manufactured at a low cost.

SUMMARY OF THE INVENTION

We have discovered a hair rinsing composition containing a substance that has a good compatibility with an aqueous solution of a cationic surface active agent and has good effects of imparting smoothness and softness to hairs. In particular, we discovered that when a certain alcohol ethoxylate formed by adding ethylene oxide to a long-chain alcohol is used in combination of a small amount of a solvent, a transparent hair rinsing composition can be obtained and this alcohol ethoxylate is comparable to or is superior to the customarily used oils and fats with respect to the effects of imparting smoothness and softness to hair. Based on this finding, we have now completed this invention.

More particularly, in the present invention, as a substance having the inherent properties of oils and fats and a surface activating property and which possesses excellent compatibility with a quaternary ammonium salt, there is used at least one member selected from the group consisting of (1) polyoxyethylene alkyl and alkenyl ethers having 8 to 20 carbon atoms in the alkyl or alkenyl group and (2) polyoxyethylene alkyl phenyl ethers having 6 to 12 carbon atoms in the alkyl group, in which the average value of the number of moles of ethylene oxide units added to (1) and (2) is in the range of from 1 to 7, and the content of the unreacted alcohol used to make (1) and (2) is reduced to a level lower than 3 wt.%. By blending this specific alcohol ethoxylate with a quaternary ammonium salt, there is obtained a transparent and stable composition which possesses excellent properties of imparting smoothness and softness to hair, and in which the foregoing described defects of conventional transparent hair rinsing compositions are obviated.

More specifically, in accordance with the present invention, there is provided a transparent hair rinsing composition comprising, as critical ingredients (A) from 0.1 to 10% by weight of at least one member selected from quaternary ammonium salts having the formula (I):

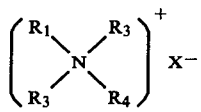

wherein $R_1$, $R_2$, $R_3$ and $R_4$ each is alkyl, hydroxyalkyl or benzyl, with the provisos that one or two of $R_1$, $R_2$, $R_3$ and $R_4$ are long-chain alkyl or hydroxyalkyl having 8 to 20 carbon atoms and the remaining two or three of $R_1$, $R_2$, $R_3$ and $R_4$ are selected from alkyl and hydroxyalkyl having 1 to 3 carbon atoms and benzyl, and X is halogen, preferably chlorine or bromine, or alkyl sulfate having 1 or 2 carbon atoms, (B) from 0.1 to 10% by weight of at least one member selected from non-ionic surface active agents having the formulas (II) and (III):

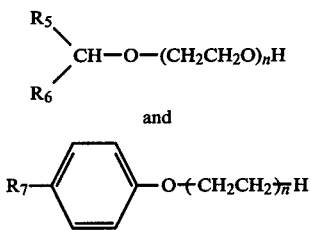

wherein $R_5$ is alkyl or alkenyl having 7 to 19 carbon atoms and $R_6$ is hydrogen or alkyl or alkenyl having 1 to 10 carbon atoms, with the proviso that the sum of the number of carbon atoms of $R_5$ plus $R_6$ is in the range of from 7 to 19, $R_7$ is a linear or branched alkyl having 6 to 12 carbon atoms, and n is the average value of the number of moles of ethylene oxide units added, as calculated with respect to mixtures of compounds having the formulas (II) or (III), wherein n is in the range of from 1 to 7, with the further proviso that the content of the compound or compounds in which n is zero in the mixture is lower than 3 wt.% based on the total weight of compounds of formula (II) or (III), and (C) from 5 to 30% by weight of a solvent selected from the group consisting of lower monohydric alcohols, polyhydric alcohols and glycols.

The quaternary ammonium salts having the formula (I) are commonly used as effective components for imparting rinsing effects in conventional hair rinsing compositions. As such quaternary ammonium salts, there can be mentioned, for example, distearyl dimethyl ammonium chloride, stearyl trimethyl ammonium methylsulfate, cetyl triethyl ammonium bromide and stearyl dimethyl benzyl ammonium chloride. In general, these salts are poorly soluble in water and it is impossible to prepare transparent aqueous solutions directly from these salts.

The non-ionic surface active agent of the formula (II) or formula (III) that is used in the present invention is prepared by adding ethylene oxide to a linear or branched higher alcohol having 8 to 20 carbon atoms or to an alkyl phenol having 6 to 12 carbon atoms in the alkyl group and wherein the unreacted alcohol or alkyl phenol is removed from the resulting adduct by distillation or the like. In general, an ethylene oxide adduct of a higher alcohol is obtained by adding ethylene oxide to the alcohol or alkyl phenol in the presence of an acid or alkali catalyst. Adducts having about 1 to about 100 moles of added ethylene oxide units are commercially available and they are used as emulsifiers, swelling agents and the like. When the above addition reaction is carried out using an alkali catalyst which is the most popularly used process on an industrial basis, there are obtained products in which the distribution range of the number of moles of added ethylene oxide units is very broad. When such products are prepared so as to have a small number of added ethylene oxide units, as used in the present invention, the unreacted alcohol (namely, the product in which the mole number of added ethylene oxide units is zero) is contained in a large amount exceeding 30 wt.%. When an acid catalyst is used for the addition reaction, there can be obtained an adduct having a substantially regular distribution of the mole number of added ethylene oxide units, but also in case of this product, the unreacted alcohol is contained in a considerably large amount. In the present invention, if there is used an adduct containing the unreacted alcohol in such a large amount, a transparent composition is not obtained. In order to obtain a transparent composition, it is necessary to use an adduct in which the content of the unreacted alcohol is reduced below 3 wt.% by distillation or the like. If the unreacted alcohol is present in an amount exceeding 3 wt.% in the adduct, it is difficult to obtain a transparent and stable composition, and in this case, a large amount of a solvent must be used to render the composition transparent. If the average mole number of added ethylene oxide units exceeds 7, the hydrophilic property is degraded and the effect of imparting smoothness and softness to hair is lowered. As a result, a rinsing composition having a high rinsing effect cannot be obtained. The amount of the adduct incorporated in the hair rinsing composition according to the invention is from 0.1 to 10% by weight, preferably 1.0 to 5.0% by weight.

In the present invention, in order to enhance the transparency in the resulting rinsing composition, it is necessary to use a solvent selected from lower monohydric alcohols such as ethanol and isopropyl alcohol, polyhydric alcohols such as glycerin and sorbitol and glycols such as ethylene glycol, propylene glycol, hexylene glycol, diethylene glycol, cellosolve and ethyl carbitol. However, the amount incorporated of such solvent necessary for achieving high transparency while maintaining the rinsing effects at high levels is much reduced as compared with the amounts of solvents used in conventional transparent rinsing compositions. In general, the solvent is incorporated in an amount of at least 5% by weight, preferably 10 to 20% by weight, and the solvent need not be incorporated in a large amount exceeding 30% by weight. Satisfactory results can be obtained even if the solvent is incorporated in a relatively small amount.

The hair rinsing composition of the present invention is prepared by dissolving the foregoing ingredients in water. If desired, conventional additives for hair rinsing compositions such as fungicides, perfumes and dyes can be added to the rinsing composition of the present invention, in the customary amounts. It is permissible to add other oils and fats if the amounts thereof are small, for example, up to 1.0 weight percent.

In order to illustrate the features of the present invention more clearly, the results of comparative tests made on the hair rinsing composition of the present invention and conventional hair rinsing compositions with respect to their rinsing effects will now be described. In the description given hereinafter, all references to "parts" and "%" are by weight.

EXPERIMENT 1

The hair rinsing compositions set forth below were prepared, and they were compared with one another with respect to the rinsing effects. The rinsing effects were evaluated according to the method described hereinafter. The results obtained are shown in Table 1.

| Compositions | |
|---|---|
| Conventional hair rinsing composition of the emulsion type (sample A): | |
| Stearyl benzyl dimethyl ammonium chloride | 2.0% |
| Cetyl alcohol | 3.0% |
| Propylene glycol | 10.0% |
| Water | 84.0% |
| Polyoxyethylene cetyl ether ($\overline{EO}$ = 10 moles) | 1.0% |
| Transparent hair rinsing composition (rendered transparent by omitting oils and fats) (sample B): | |
| Stearyl benzyl dimethyl ammonium chloride | 4.0% |
| Propylene glycol | 10.0% |
| Water | 86.0% |
| Hair rinsing composition of the present invention (sample C): | |
| Stearyl trimethyl ammonium chloride | 2.0% |
| Secondary alcohol ethoxylate ($\overline{C}$ = 13, $\overline{EO}$ = 3 moles, unreacted alcohol content = 1.0%) | 2.0% |
| Propylene glycol | 10.0% |
| Water | 86.0% |

Notes
$\overline{C}$ means average carbon number
$\overline{EO}$ means average mole number of added ethylene oxide units.

Evaluation of Rinsing Effects

A human hair bundle having a length of 15 cm and a diameter of 2 cm was dipped for 5 seconds in 200 cc of a 2% aqueous solution of the hair rinsing composition maintained at 40° C. Then, the hair bundle was rinsed for 30 seconds with 200 cc of warm water maintained at 40° C. two times, and it was naturally dried. The touch and feel, the suppleness, the softness and the smoothness were examined by a panel of 10 women to evaluate the rinsing effects.

Table 1

| Combinaton of Samples Compared | Evaluation of Rinsing Effects Number of Persons | | | |
|---|---|---|---|---|
| | A is better | B is better | C is better | No difference |
| A-B | 7 | 2 | — | 1 |
| A-C | 2 | — | 6 | 2 |
| B-C | — | 0 | 10 | 0 |

As will be apparent from the results shown in Table 1, the rinsing composition of the present invention (sample C) is much superior to the conventional transparent composition (sample B) and is superior to the conventional emulsion type composition (sample A) with respect to the rinsing effects.

EXPERIMENT 2

Various polyoxyethylene alkyl ethers were incorporated in a basic hair rinsing composition, and the rinsing effects were evaluated in the same manner as described in Experiment 1. The results obtained are shown in Table 2.

| Basic Composition | |
|---|---|
| Stearyl trimethyl ammonium chloride | 3.0% |
| Secondary alcohol or ethoxylate thereof (average carbon number $\overline{C}$ = 13.2) | 2.0% |
| Propylene glycol | 20.0% |
| Water | 75.0% |

| Secondary Alcohol Ethoxylates Tested | |
|---|---|
| Mole number of added ethylene oxide | Sample Identification |
| 0 (secondary alcohol) | X |
| 1 | D |
| 2 | E |
| 3 | F |
| 4 | G |
| 5  secondary alcohol ethoxylate | H |
| 6 | I |
| 7 | J |
| 8 | K |
| 10 | L |

Table 2

| | Evaluation of Rinsing Effects (based on sample F as standard for comparison) | | |
|---|---|---|---|
| Combination of Samples Compared | Number of Persons | | |
| | Sample F is better | No difference | Other sample is better |
| F-X | no transparent sample was obtained | | |
| F-D | 4 | 3 | 3 |
| F-E | 3 | 4 | 3 |
| F-G | 5 | 1 | 4 |
| F-H | 5 | 2 | 3 |
| F-I | 7 | 1 | 2 |
| F-J | 8 | 0 | 2 |
| F-K | 10 | 0 | 0 |
| F-L | 10 | 0 | 0 |

As will readily be understood from the results shown in Table 2, the rinsing effects are gradually degraded as the number of moles of added ethylene oxide increases, and if the mole number is 8 or larger, no substantial rinsing effects can be obtained. When the mole number is zero, no transparent composition is obtained.

The following are representative examples of compositions according to the invention.

EXAMPLE 1

| Stearyl trimethyl ammonium chloride | 3.0% |
|---|---|
| Lauryl alcohol ethoxylate (EO = 3.0) | 2.0% |
| (unreacted lauryl alcohol content = 1.5%) | |
| Ethyl alochol | 5.0% |
| Propylene glycol | 10.0% |
| Perfume and dyes | small amounts |
| Deionized water | 80.0% |

EXAMPLE 2

| Cetyl trimethyl ammonium chloride | 4.0% |
|---|---|
| Isostearyl alcohol ethoxylate ($\overline{EO}$ = 3.5) | 3.0% |
| (unreacted isostearyl alochol content = 1.5%) | |
| Isopropyl alcohol | 5.0% |
| Propylene glycol | 15.0% |
| Perfume and dye | small amounts |
| Deionized water | 73.0% |

EXAMPLE 3

| Stearyl dimethyl benzyl ammonium chloride | 2.0% |
|---|---|

-continued

| | |
|---|---|
| Oleyl alcohol ethoxylate ($\overline{EO}$ = 4.0) | 4.0% |
| (unreacted oleyl alcohol content = 1.0%) | |
| Ethyl alochol | 5.0% |
| Propylene glycol | 15.0% |
| Perfume and dye | small amounts |
| Deionized water | 74.0% |

EXAMPLE 4

| | |
|---|---|
| Distearyl dimethyl ammonium chloride | 1.0% |
| Stearyl trimethyl ammonium chloride | 2.0% |
| Hexadecyl alcohol ethoxylate ($\overline{EO}$ 5.0) | 3.0% |
| (unreacted hexadecyl alcohol content = 0.5%) | |
| Ethyl alcohol | 7.0% |
| Propylene glycol | 13.0% |
| Perfume and dye | small amounts |
| Deionized water | 74.0% |

Each of the foregoing compositions of Examples 1 to 4, as well as sample C prepared in Experiment 1, had excellent rinsing effects and was superior to conventional hair rinsing compositions with respect to the rinsing effects. Further, even after they had been allowed to stand at −5° C. for one month, the transparent state was maintained in each composition.

The embodiments of the invention in which an exclusive property or privilege is claimed are defined as follows:

1. A transparent liquid hair rinsing composition consisting essentially of
(A) from 0.1 to 10% by weight of one or a mixture of quaternary ammonium salts having the formula (I):

$$\left[ \begin{array}{c} R_1 \diagdown \diagup R_3 \\ N \\ R_2 \diagup \diagdown R_4 \end{array} \right]^+ X^-$$
(I)

wherein $R_1$, $R_2$, $R_3$ and $R_4$ each is alkyl, hydroxyalkyl or benzyl, with the proviso that one or two of $R_1$, $R_2$, $R_3$ and $R_4$ is long-chain alkyl or hydroxyalkyl having 8 to 20 carbon atoms and the remaining groups are selected from alkyl and hydroxyalkyl having 1 to 3 carbon atoms and benzyl, and X is halogen or alkyl sulfate having 1 or 2 carbon atoms, (B) from 0.1 to 10% by weight of non-ionic surface active agent having the formulas (II) or (III):

$$\begin{array}{c} R_5 \diagdown \\ CH-O-(CH_2CH_2O)_{\overline{n}}-H \\ R_6 \diagup \end{array}$$
(II)

and $$R_7 - \bigcirc - O-(CH_2CH_2O)_{\overline{n}}-H$$
(III)

and mixtures thereof, wherein $R_5$ is an alkyl or alkenyl having 7 to 10 carbon atoms and $R_6$ is hydrogen or alkyl or alkenyl having 1 to 10 carbon atoms, with the proviso that the sum of the numbers of carbon atoms of the groups $R_5$ plus $R_6$ is in the range of from 7 to 19, $R_7$ is linear or branched alkyl having 6 to 12 carbon atoms, and n is the average value of the number of moles of added ethylene oxide units and is in the range of from 1 to 7, with the further proviso that the content of compound in which n is zero is lower than 3% based on the total weight of ingredient B,
(C) 5 to 30% by weight of a solvent selected from the group consisting of lower monohydric alcohols, polyhydric alcohols and glycols, and
(D) the balance is essentially water.

2. A transparent liquid hair rinsing composition as set forth in claim 1 wherein the solvent is one member or a mixture of members selected from the group consisting of ethanol, isopropyl alcohol, ethylene glycol, propylene glycol, glycerin and xylene glycol.

3. A transparent liquid hair rinsing composition as set forth in claim 1 wherein the amount of the solvent (C) is 10 to 20% by weight.

4. A transparent liquid hair rinsing composition as set forth in claim 3 wherein the content of the quaternary ammonium salt (A) is 1 to 5% by weight and the content of the non-ionic surface active agent (B) is 1 to 5% by weight.

5. A transparent liquid hair rinsing composition as set forth in claim 2 in which said nonionic surface active agent (B) consists of the formula III substance.

6. A transparent liquid hair rinsing composition as set forth in claim 2 in which said nonionic surface active agent (B) consists of the formula II substance.

7. A transparent liquid hair rinsing composition as set forth in claim 2 in which n is in the range of from 1 to 5.

* * * * *